United States Patent [19]

Cho

[11] Patent Number: 5,641,514
[45] Date of Patent: Jun. 24, 1997

[54] CEMENT BEAD COMPOSITION FOR ORTHOPAEDIC SURGERY AND ITS MANUFACTURING PROCESS

[76] Inventor: Se Hyun Cho, Da-dong 608 Hyundai Apartment 277 Chilam-dong, Chinju-city Kyeongsangnam-do, Rep. of Korea, 660-702

[21] Appl. No.: 380,863

[22] Filed: Jan. 30, 1995

[30] Foreign Application Priority Data

Jan. 29, 1994 [KR] Rep. of Korea ............... 1632/1994
Jan. 11, 1995 [KR] Rep. of Korea ............... 382/1995

[51] Int. Cl.$^6$ ................................................ A61K 9/14
[52] U.S. Cl. ................................... 424/487; 424/501
[58] Field of Search ........................ 523/116; 424/488, 424/489, 490, 487, 501

[56] References Cited

U.S. PATENT DOCUMENTS

| 4,277,184 | 7/1981 | Solomon | 366/150 |
| 4,460,279 | 7/1984 | Krasney | 366/247 |
| 5,334,626 | 8/1994 | Lin | 523/116 |

OTHER PUBLICATIONS

The Journal of Bone and Joint Surgery vol. 60–B, No. 2, pp. 270–275 (1978).
The Journal of Bone and Joint Surgery vol. 64–B, No. 4, pp.460–464 (1982).
The Journal of Bone and Joint Surgery vol. 70–A, No. 10, pp.1551–1557 (1988).
The Journal of Bone and Joint Surgery vol. 63–A, No. 5, pp. 798–804 (1981).

*Primary Examiner*—Thurman K. Page
*Assistant Examiner*—William E. Benston, Jr.
*Attorney, Agent, or Firm*—Jacobson, Price, Holman & Stern, PLLC

[57] ABSTRACT

The present invention relates to cement bead for orthopaedic surgery and its manufacturing process, embodying the cement beads for orthopaedic surgery manufactured from the mixture of antibiotics and cement which can be implanted into the dead space produced after the first saucerization on a patient with chronic osteomyelitis.

Thus, the present invention is designed to obtain direct bactericidal effect by implanting the cement beads into a dead space, produced after the first saucerization, and to reduce the toxicity of systemic antibiotics and the risk of recurrence by mixing broad spectrum antibiotics, being thermally stable and sensitive to many microorganisms, where it comprises; mixing Ticarcillin of 5–10 g, Cefazolin of 5–10 g, Tobramicin of 5–10 g and Vancomycin of 5 g; homogenizing 20–25 cc of antibiotic mixed powder with 120 cc of powder cement; mixing this homogenized powder with 20–30 cc of liquid cement; cutting it in the form of rosary in the process of hardening; running a needle and thread through them to make the chain of antibiotic-mixed cement beads.

5 Claims, No Drawings

CEMENT BEAD COMPOSITION FOR ORTHOPAEDIC SURGERY AND ITS MANUFACTURING PROCESS

FIELD OF THE INVENTION

The present invention relates to making cement bead composition for orthopaedic surgery and its manufacturing method and more particularly, to a method of using cement beads mixed with antibiotics, which are effective in the treatment of acute and chronic osteomyelitis and various infections of musculoskeletal system.

DESCRIPTION OF THE PRIOR ART

Chronic osteomyelitis has been known as one of difficult diseases to treat in orthopaedic field because it often shows high incidence of recurrence and resistance to treatment by producing organisms resistant to antibiotics, producing adverse drug reactions from habitual and long-term administration of antibiotics.

However, it seems that at present the incidence of chronic osteomyelitis is increasing due to incresing trauma or open fracture from traffic accidents and industrial injuries compared with the past when acute osteomyelitis used to be its major cause (J. of Korean Orthop. Assoc. 24: 549–556, 1989).

Chronic osteomyelitis has always been a clinical dilemma in respect of resistance to treatment and frequent liability of recurrence. Besides, many factors may play a role for the difficulty in treatment such as periosteal hypertrophy, sclerotic cortex, sequestrum and scar tissue with poor vascularity surrounding the bone. Hitherto, a variety of treatment methods have been proposed to overcome those problems.

Saucerization, which is an essential method to eradicate the infected and sequestrated part of bone, has long been widely accepted as a method of surgery for chronic osteomyelitis. However, some controversies have arisen regarding the management of dead space, which is always produced after saucerization, such as muscle pedicle graft, continuous irrigation and vaselin gauze insertion.

Curettage, extensively performed to thoroughly treat osteomyelitis, always produces the dead space and its management is one of important parameters which decide the end result of the treatments.

In 1970, Buchholz and Engelbrecht first used gentamicin containing bone cement in the fixation of total hip implant to bone for the prevention of postoperative infection based on the expectation that cement might release antibiotics for a certain period of time (Buchholz. H. W., und Engelbrecht, H.: Uber die Depotwirkung einiger Antibiotica bei Vermischung mir dom Kunstharz Palaces, Chirurg, 41: 511–515, 1970).

Klemm in 1976 and Wahlig in 1978 reported satisfactory result from treatment of chronic osteomyelitis by implantation of gentamicin containing cement beads at the dead space after saucerization (Klemm, K: Treatment of chronic bone infection with gentamicin-PMMA beads, Accident Surg., 16:5–7, Special Issue; Gentamicin-PMMA beads, 1976) (Wahlig, H., Dingeldein, E.,Bergamann, R. and Reuss, K.: The release of gentamicin from polymethylmethacrylate beads. J. Bone und Joint Surg., 60-B: 270–275, 1978).

The mechanism of antibiotic release from cement beads is another controversy. Antibiotics are believed to be released around the beads by diffusion which may happen parallel to the concentration gradient according to Bayston, Klemm and Buchholz (Bayston, R. and Milner, R. D. G.: The sustained release of antimicrobial drugs from bone cement. J. Bone and Joint Surg., 64-B: 460–464, 1982). But Baker et al. suggested that antibiotic is released by direct flow through an interconnecting series of voids and cracks in cement, rather than through diffusion (Baker, A. S. and Greenham, L. W.: Release of gentamicin from acrylic bone cement. J. Bone and Joint Surg., 70-A: 1551–1557, 1988).

There are also different opinions about the duration of antibiotic release. Maximal concentration of antibiotics in tissue fluid after implantation was meaured at one or three hours postoperatively and antibacterial effect lasted one or three weeks (Pickneil, B., Mizen, L. and Sutherland, R.: Antibacterial activity of antibiotics in acrylic bone cement. J. Bone and Joint Surg., 59-B: 302–307, 1977). Hoff et al. also reported its effect lasted as long as seven months (Hoff, S. F., Fitzgerald, R. B. and Kelly, P. J.: The depot administration of Penicillin G and gentamicin in acylic bone cement. J. Bone and Joint Surg. 63-A: 798–804, 1981).

It has been elucidated that cement beads used, which contained simply gentamicin or other two or three kinds of antibiotics, prepared directly by physicians in operating room, thus had several disadvantages as the followings ; the sensitivity to bacteria was limited; the concentration in each cement bead was not uniform; the method was used for merely experimental preparation, it couldn't be used for manufacturing in a commercial scale.

DETAILED DESCRIPTION OF THE INVENTION

It is an object of the present invention to manufacture antibiotic-mixed cement beads on a commercial scale, being sensitive to as many causative microorganisms as possible.

The present invention had been clinically applied as follows.

In 31 patients with chronic osteomyelitis, causative microorganisms were identified by bacterial culture as shown in the Table 1.

The identification of distribution of causative microorganisms was followed by the selection of proper antibiotic, being sensitive to most of them and thermal stability to heat produced during bead preparation. The proper antibiotics and mixing ratio are shown as in Table 2.

TABLE 1

| Causative Microorganism of Chronic Osteomyelitis | |
| --- | --- |
| Microorganism | No. of Cases |
| *Staphylococcus aureus* | |
| Coagulase (+) | 21 |
| Coagulase (−) | 2 |
| Pseudomonas | 9 |
| Enterobacter | 5 |
| *E. coli* | 3 |
| Group D streptococcus | 1 |
| Serratia | 2 |
| *Proteus vulgaris* | 1 |
| Acinetobacter | 2 |
| None | 10 |

TABLE 2

Antibiotic Bead Cocktails

| | |
|---|---|
| 1) Penicillins, Ticarcillin | 5–10 g |
| 2) Cephalosporins, Cefazolin | 5–10 g |
| 3) Aminoglycosides, Tobramycin | 5–10 g |
| 4) Vancomycin | 5 g |

Four antibiotic powders, selected according to the sensitivity results, were thoroughly mixed under sterile conditions and then homogenously mixed with the powder cement (polymethylmethacrylate). The powder cement, a commercial product with a packing unit of 40 g(120 cc), should be mixed with antibiotics at the volumetric ratio of 20–25:120, it prefers to mix 20 to 25 cc of antibiotics with 120 cc of powder cement, since excess than 25 cc of antibiotics makes it difficult to harden cement.

This powder mixture of antibiotics and cemement is mingled with 20 to 30 cc of liquid cement (Methylmethacrylate monomer).

During this hardening process, cement beads in the form of rosary are prepared by cutting them of about 5 mm in diameter, and followed by running a needle and thread through them to obtain cement beads containing antibiotics according to the invention.

The number of cement beads depends on the size of dead space produced by curettage and is usually about from 50 to 200. The concentration of released antibiotics from the beads, estimated 30 days after implantation was up to 60 times of MBC(Minimal Bactericidal Concentration), showing the sufficient bactericidal effect and as no systemic toxicity due to negligible concentration of antibiotics in blood.

The invention is described more in detail by the examples of manufacturing cement beads and treatment using them as set forth hereunder.

[Example of preparation]

Ticarcillin of 5 g, Cefazolin of 5 g, Tobramycin of 5 g and Vancomycin of 5 g were thoroughly mixed under sterile conditions to obtain 25 cc of powder mixture of antibiotics and then powder cement (Polymethyl methacrylate resin, PMMA) of 40 g(120 cc) was added to them and homogenized.

Homogenized powder was mixed with 30 cc of liquid cement (Methylmethacrylate monomer), stirred leading to slow hardening with time, and in the middle of dough phase, beads were cut in the size of diameter of 5 mm and in the form of rosary, to obtain about one hundred cement beads, followed by running a needle and thread through them.

[Example of treatment]

31 patients with chronic osteomyelitis were selected for this treatment.

Distribution of their ages and sexes is shown as in Table 3.

TABLE 3

Distribution of Age and Sex

| Age | Male | Female | Total |
|---|---|---|---|
| 11–20 | 1 | 1 | 2 |
| 21–30 | 4 | 1 | 5 |
| 31–40 | 8 | 3 | 11 |
| 41–50 | 5 | 2 | 7 |

TABLE 3-continued

Distribution of Age and Sex

| Age | Male | Female | Total |
|---|---|---|---|
| 51–60 | 3 | 1 | 4 |
| Over 61 | 1 | 1 | 2 |
| Total | 22 | 9 | 31 |

The duration of disease (from the occurrence of disease to operation with cement bead) is shown as Table 4 below.

TABLE 4

Duration of Disease

| Duration | No. of Cases |
|---|---|
| 6 months–2 yrs | 13 |
| 2–5 yrs | 11 |
| 5–10 yrs | 3 |
| Over 10 yrs | 4 |
| Total | 31 |

The cause of chronic osteomyelitis is shown as below Table 5.

TABLE 5

Cause of Chronic Osteomyelitis

| Causes | No. of Cases |
|---|---|
| Hematogenous Osteomyelitis | 13 |
| Open fracture | 11 |
| Postoperative infection | 3 |
| Penetrating injury | 1 |
| Gunshot injury | 1 |
| Unknown | 2 |
| Total | 31 |

The number of cases according to the location of lesion is shown as below Table 6.

TABLE 6

Location of Lesion

| Location | No. of Cases |
|---|---|
| Tibia | 14 |
| Femur | 12 |
| Humerus | 2 |
| Radius | 2 |
| Calcaneus | 1 |
| Total | 31 |

[Surgical procedure]

In 31 patients with chronic osteomyelitis, saucerization was performed with an effort of minimizing vascular injury following the debridement of soft tissue, by the incisions carefully lining between myocutaneous territories.

Antibiotic-mixed cement beads, prepared according to the invention, were implanted into the dead space and wound was closed.

The cement beads were removed within about four weeks and the dead space was replaced by fresh bone grafts.

[Results of treatment]

Results of treatment were very satisfactory;

17 cases were completely recovered from chronic osteomyelitis and the other 10 cases recurred. But showed very clean dead space, ensuring the antibacterial effect of cement beads. Seven cases out of ten recurrences were cured simply by curettage and three required curettage and bone graft. It was a pity that the remaing four cases had to be amputated due to complication of pathologic fracture or squamous cell carcinoma.

Table 7 shows the results of treatment.

TABLE 7

Results of Treatment

| Results | No. of Cases |
|---|---|
| Cured | 17 |
| Recurred but Improved by | |
| a) curettage | 7 |
| b) curettage and bone graft | 3 |
| Amputated | 4 |
| Total | 31 |

As discussed above, in case that cement beads according to the invention were used after saucerization, its effectiveness in treatment of chronic osteomyelitis was excellent, lasting the bactericidal effect on the surrounding dead space for a long time.

The conventional method of systemic administration of antibiotics leaving the dead space as it is, had often been a failure with the economic loss, systemic toxicity by long-term administration, and the high recurrence rate.

The advantages of antibiotic-mixed cement beads according to the present invention are summarized as follows;

(1) As no or only a small amount of antibiotics are administered systemically, there is little side effect.

(2) It is economical because it is unnecessary to administer the expensive antibiotics for a long time.(Namely, the medical cost can be saved.)

(3) Implantation of cement beads and closure of the wound make dressing simple and the period of hospitalization short (namely, the saving of hopitalization cost is expected).

(4) The poor vascularity around the tissue area of chronic osteomyelitis prevents effective approach of antibiotic even though antibiotic is administered systemically in high concentration. But, the present invention has a direct bactericidal effect due to implantation into the dead space.

(5) It was found that a large amount of antibiotic, enough to sterilize the surrounding bone after saucerization, was released from cement beads.

Therefore, the present invention must be very excellent and effective in the treatment of bone and joint infections.

I claim:

1. Cement beads for orthopaedic surgery comprising: 20–25 cc of antibiotic mixed powder consisting essentially of 5–10 g of Ticarcillin, 5–10 g of Cefazolin, 5–10 g of Tobramycin and 5 g of Vancomycin; 120 cc of powder cement; and 20–30 cc of liquid cement; wherein the powder cement is polymethylmethacrylate and the liquid cement is methylmethacrylate monomer.

2. A process for manufacturing antibiotic-mixed cement beads for orthopaedic surgery comprising the steps of mixing 5–10 g Ticarcillin, 5–10 g of Cefazolin, 5–10 g of Tobramycin and 5 g of Vancomycin under sterile conditions to obtain an antibiotic mixed powder, adding 120 cc of powder cement to 20–25–cc of the antibiotic mixed powder; homogenizing the powder cement and antibiotic mixed powder to obtain an homogenized powder; mixing homogenized powder with 20–30 cc of liquid cement to obtain a cement mixture; and cutting the cement mixture to a size having a diameter of about 5 mm when the cement mixture reaches a dough phase to obtain cement beads: wherein the powder cement is polymethylmethacrylate and the liquid cement is methylmethacrylate monomer.

3. The cement beads of claim 1 wherein said beads have a diameter of about 5 mm.

4. Cement beads for orthopaedic surgery consisting essentially of 5–10 g of Ticarcillin, 5–10 g of Cefazolin, 5–10 g of Tobramycin and 5 g of Vancomycin; 120 cc of powder cement; and 20–30 cc of liquid cement.

5. The process of claim 2 further comprising running a needle and thread through the cement beads to obtain chains of antibiotic-mixed cement beads.

* * * * *